United States Patent [19]

Feamster, III

[11] 4,304,133

[45] Dec. 8, 1981

[54] POSITIONING DEVICE FOR SCANNER

[76] Inventor: William C. Feamster, III, 4013 Nina Dr., Chesapeake, Va. 23321

[21] Appl. No.: 134,891

[22] Filed: Mar. 28, 1980

[51] Int. Cl.³ ............................................. G01N 29/04
[52] U.S. Cl. ..................................................... 73/633
[58] Field of Search ................ 73/633, 618, 620, 622; 33/1 M

[56] References Cited

U.S. PATENT DOCUMENTS

| | | | |
|---|---|---|---|
| 3,323,354 | 6/1967 | Daubresse et al. | 73/620 |
| 3,434,331 | 3/1969 | Harper et al. | 33/1 M |
| 3,575,042 | 4/1971 | Lovelace et al. | 73/620 |
| 3,918,167 | 11/1975 | Gerber | 33/1 M |
| 4,013,280 | 3/1977 | Chitayat et al. | 33/1 M |
| 4,170,145 | 10/1979 | Kennedy et al. | 73/620 |

*Primary Examiner*—Anthony V. Ciarlante

*Attorney, Agent, or Firm*—Mason, Fenwick & Lawrence

[57] ABSTRACT

A manually operable scanner includes a rectangular frame having suction cups or other mounting devices connectable to a casting or other body to be scanned with a carriage being mounted on the frame for reciprocation in a first direction. A scanner such as an ultrasonic transducer is mounted on the carriage for reciprocation in a direction perpendicular to the direction of movement of the carriage with movement of the carriage and the scanner being sensed by first and second rotary encoders each of which provides an output signal to a display indicative of the position of the transducer with respect to the rectangular frame so that upon a detection of a fault in the body being scanned, the coordinates of location of the fault are immediately available from a visual readout of the coordinates from the display means.

7 Claims, 8 Drawing Figures

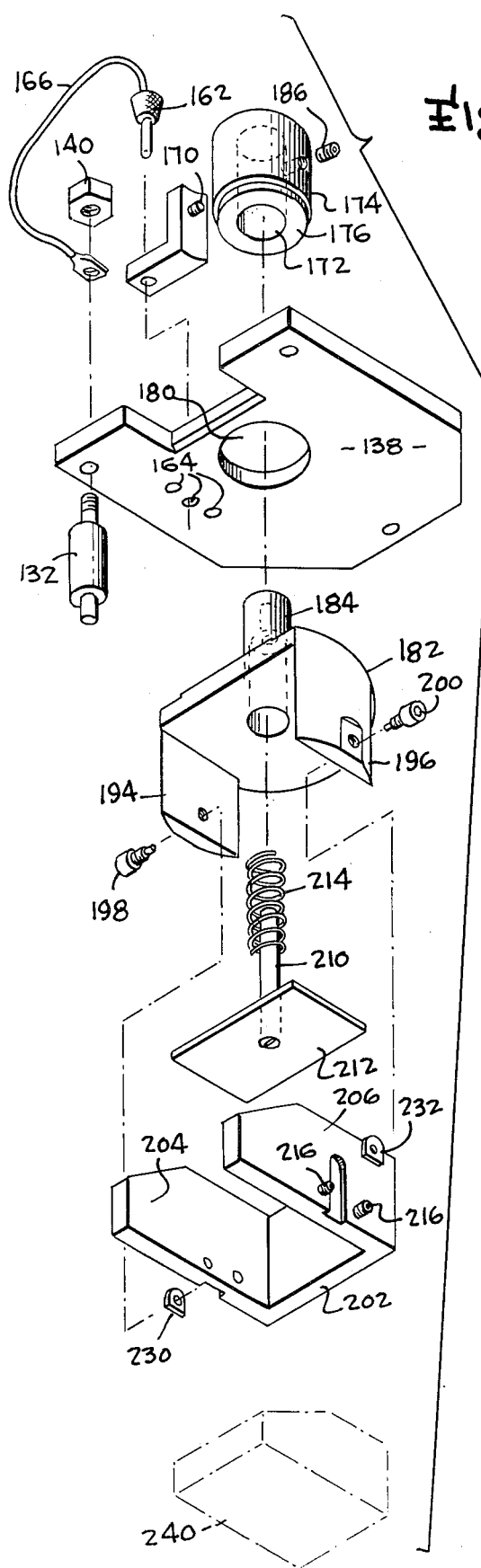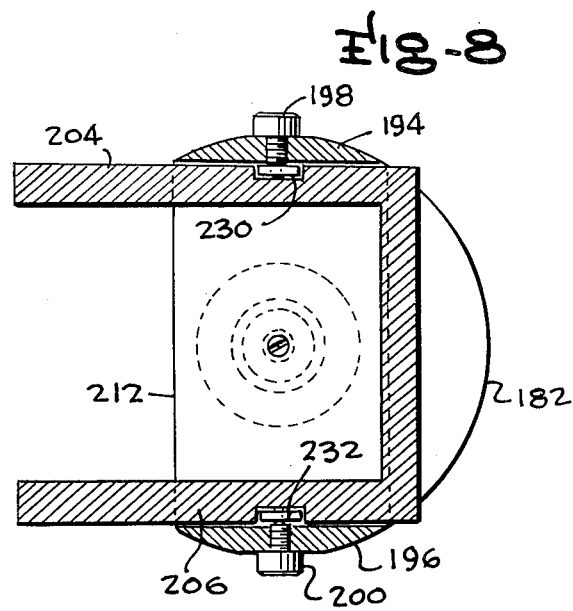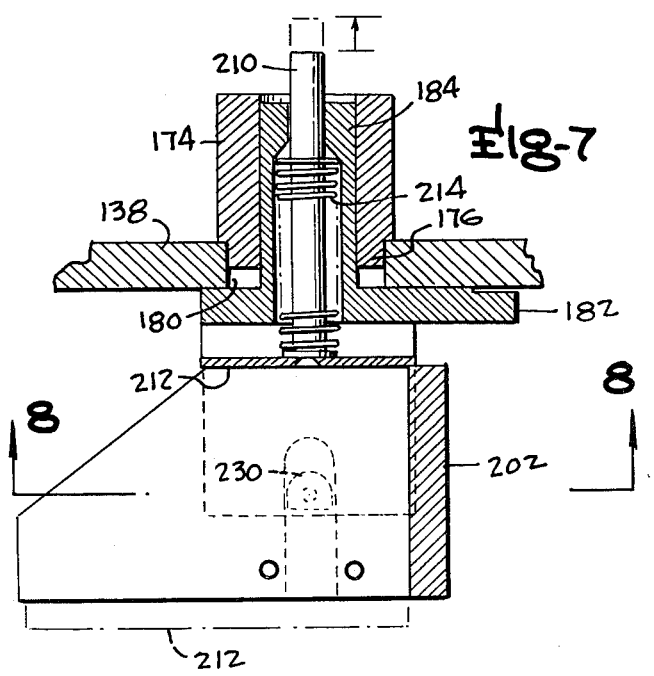

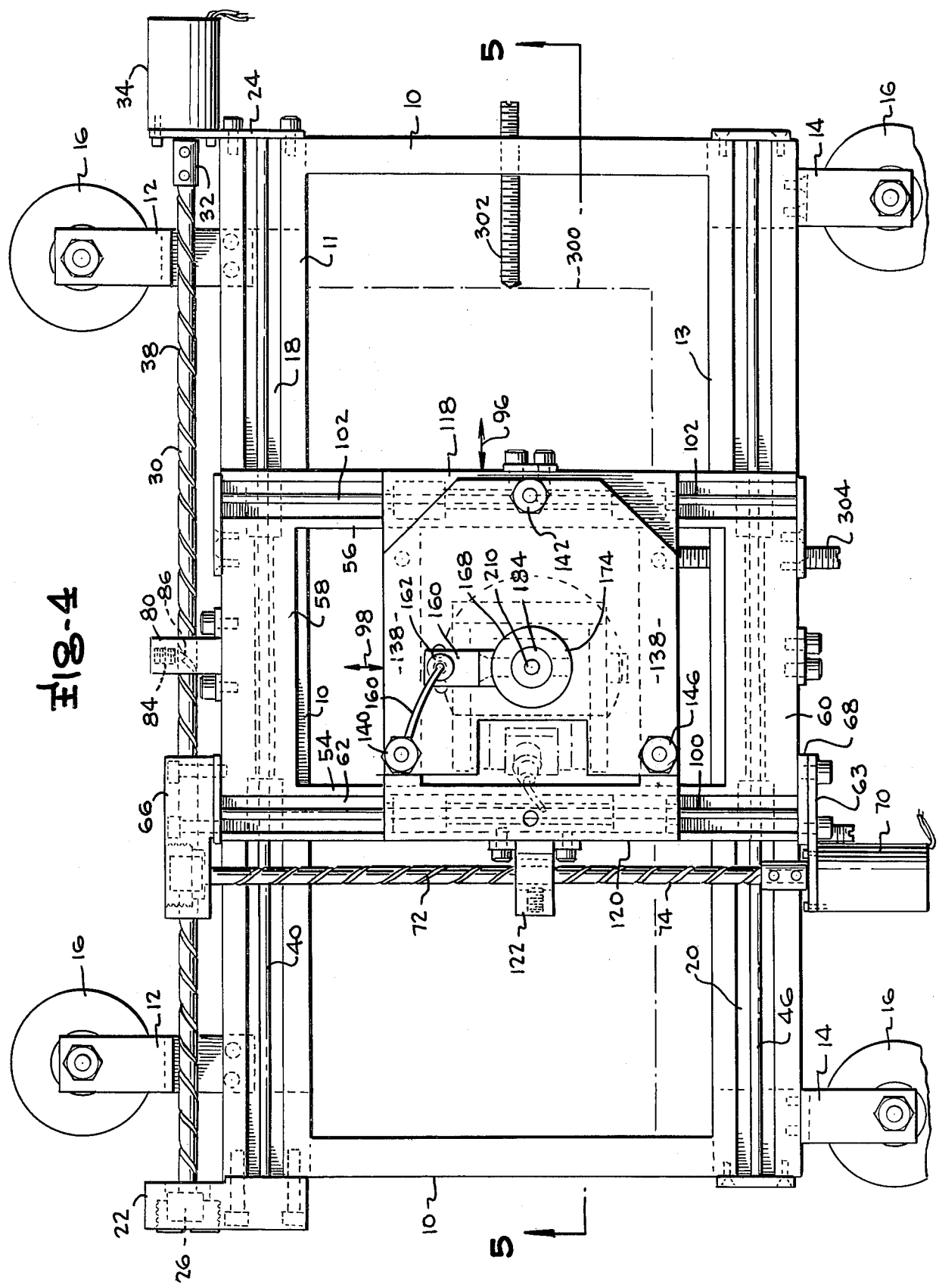

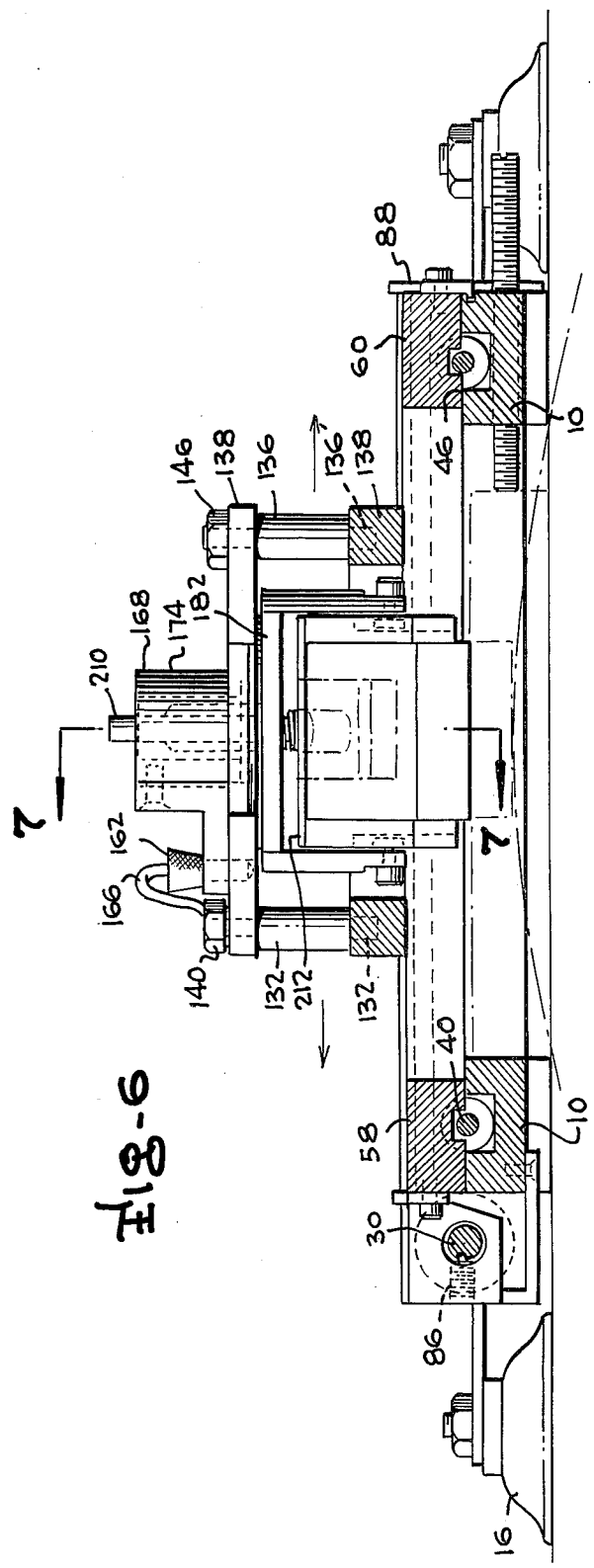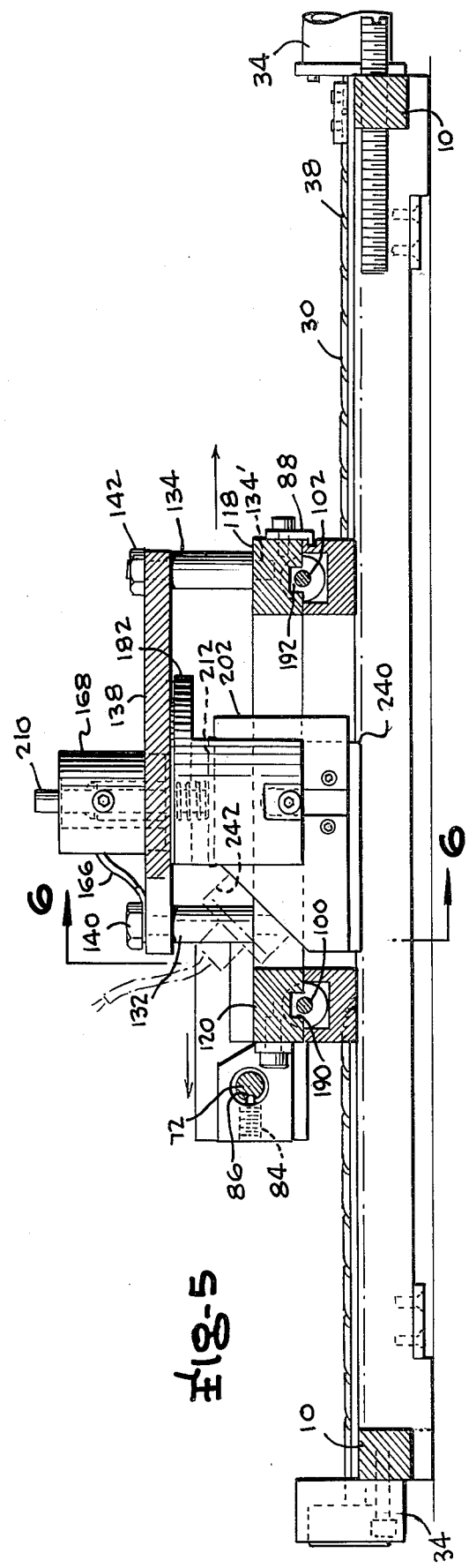

POSITIONING DEVICE FOR SCANNER

BACKGROUND OF THE INVENTION

This invention is in the field of positioning and detecting means and is more specifically directed to a scanner which is positionable on a casting or other item for locating internal flaws by means of a conventional transducer mounted on the scanner.

Prior devices have been proposed for the purpose of scanning items such as castings with such devices usually employing hand-held transducers or possibly motor driven scanner supports which progressively traverse the entire surface of a survey area of the item being inspected. Such scanners are costly and time consuming in use. There has consequently been an unmet need for a simple and portable scanner which can be manually operated for detecting the location of internal flaws in metal and other bodies repeatably. The provision of such a scanner is the primary object of this invention.

Achievement of the object of this invention is enabled through the preferred embodiment which comprises a portable frame on which a carriage is mounted for reciprocation. Reciprocation of the carriage effects rotation of a threaded rod engaged by a drive pin on the carriage with the rod driving a first rotary encoder providing an output in accordance with the extent and direction of rotation of the rod. The carriage supports a slide carrier means for reciprocation perpendicular to the direction of movement of the carriage on the frame with a transducer being mounted on the slide carriage means so that it is positioned immediately adjacent a body over which it is to be moved for scanning purposes. A second threaded rod is rotated by movement of the slide carrier means to rotate a second rotary encoder. Both encoders are connected to display members which provide a visual indication of the count in each encoder and consequently provide a visual indication of the position of the transducer along perpendicular axes at any particular moment, such as when the transducer detects a flaw in the body being scanned. It is consequently possible for the operator to immediately pinpoint the location of the flaw by noting the coordinate position of the transducer as indicated by the display members.

BRIEF DESCRIPTION OF THE DRAWINGS

FIG. 3 is an exploded perspective view of sensor supporting components of the preferred embodiment;

FIG. 4 is a top plan view of the preferred embodiment;

FIG. 5 is a sectional view taken along lines 5—5 of FIG. 4;

FIG. 6 is a sectional view taken along lines 6—6 of FIG. 5;

FIG. 7 is a sectional view taken along lines 7—7 of FIG. 6; and

FIG. 8 is a sectional view taken along lines 8—8 of FIG. 7.

DESCRIPTION OF THE PREFERRED EMBODIMENT

Figure 1:
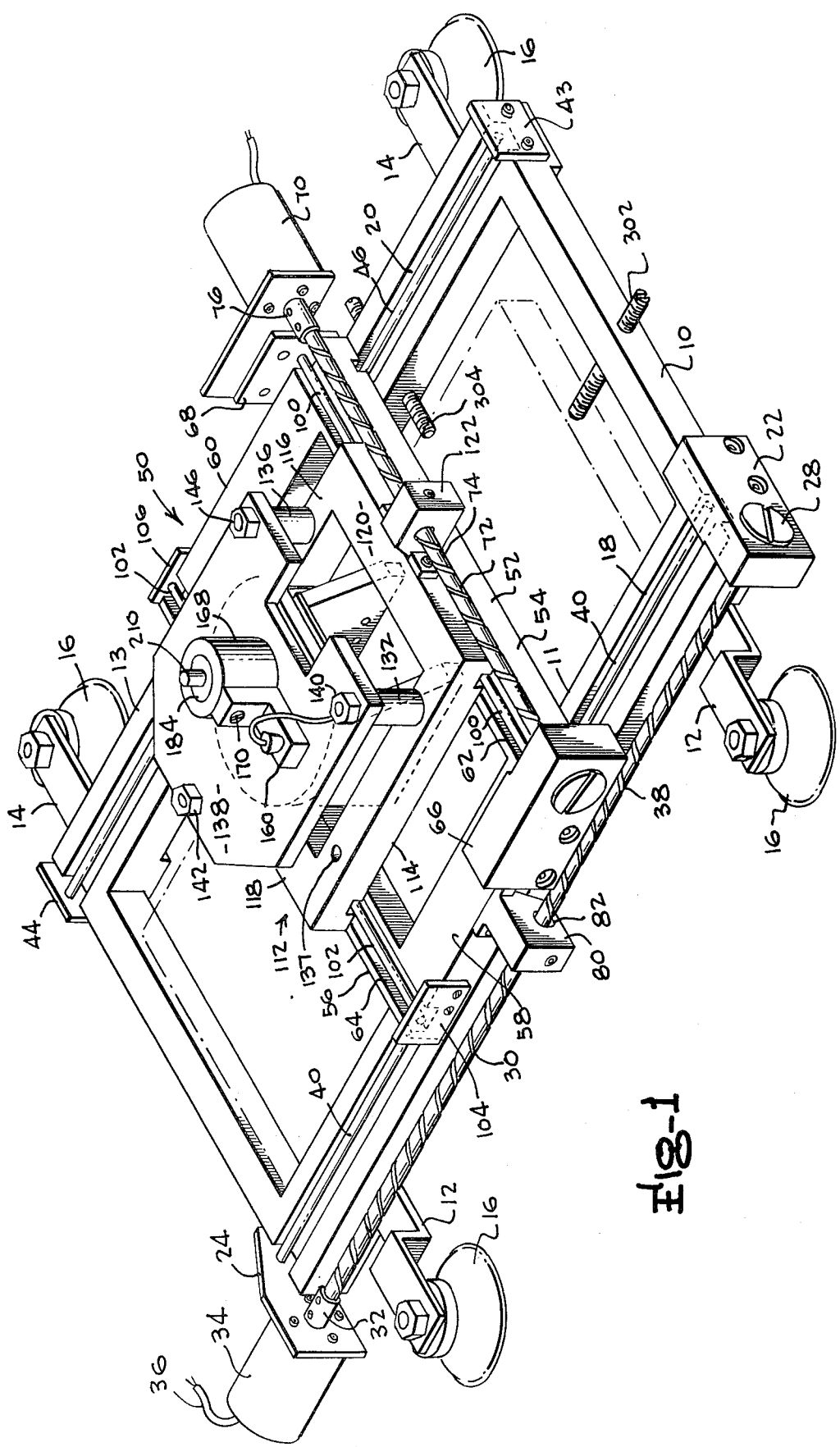
FIG. 1 is a perspective view of the preferred embodiment of the subject invention.
Figure 2:
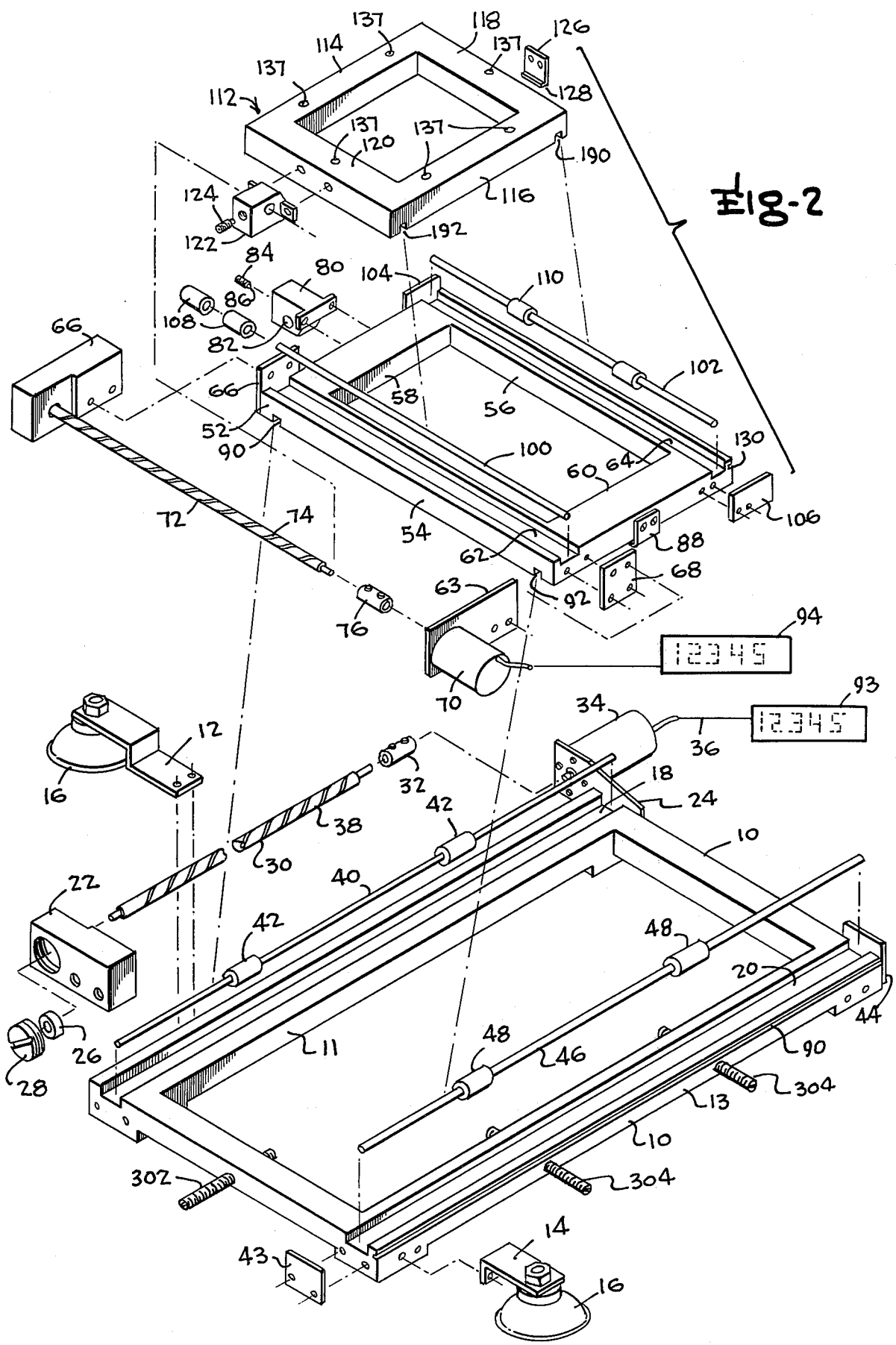
FIG. 2 is an exploded perspective view of a portion of the preferred embodiment.

Attention is initially invited to FIGS. 1 and 2 of the drawings which best illustrate the primary components of the preferred embodiment. More specifically, a portable but fixedly positionable rectangular base frame 10 formed of aluminum or other rigid material is provided with suction cup support brackets 12 attached to the frame along one side and similar suction cup support brackets 14 along its opposite side with suction cups 16 being connected to the support brackets for supporting the frame 10 in an obvious manner on a supporting surface. It should be understood that mounting means, such as magnets, other than suction cups may be employed.

Base frame 10 includes downwardly extending grooves 18 and 20 in the upper surface of its longer side portions 11 and 13. A bearing carrier block 22 and a signal generator support bracket plate 24 are attached to the base frame 10 at opposite ends of the downwardly extending groove 18. A rotary bearing 26 is provided internally of the bearing carrier block 22 and is held in position by a threaded cap 28 with bearing 26 supporting the end of a rotary drive rod 30, the opposite end of which is connected by a coupling 32 to the input shaft of a first conventional rotary input encoder 34 of the type capable of counting up or down in accordance with the direction of rotation of its input shaft with the total count being indicative of the angular sum of rotation of the input shaft. An output line 36 is connected to an indicator 93 having a visible output indicative of the instantaneous count of encoder 34 and consequently indicating a coordinate position with respect to and along a first axis parallel to the direction of movement of a carriage 50 mounted for movement on frame 10 as discussed hereinafter. Rotation of the rotary drive rod 30 is effected by later described drive pin means on carriage 50 engageable with a spiral groove 38 extending along the length of the outer surface of rod 30.

A slide bearing rod 40 is mounted in and extends along the length of downwardly extending groove 18 with the ends of rod 40 being respectively connected in the bearing carrier block 22 and the signal generator support bracket plate 24. First and second tubular slide bearings 42, of the type generally referred to as "Thompson" bearings, are mounted for low-friction reciprocation along a first directional axis on the polished slide bearing rod 40. A second slide bearing rod 46 is mounted on support bracket plates 43 and 44 attached to the fixed base frame 10 at opposite ends of the downwardly extending groove 20. Slide bearings 48 identical to slide bearings 42 are mounted on the slide bearing rod 46 for reciprocation along the length thereof. Slide bearing rods 40 and 46 constitute carriage support means for supporting carriage 50 for reciprocation in a first direction parallel to the axes of rods 40, 46 and the rotary drive rod 30.

Carriage 50 comprises a rectangular carriage frame 52 having elongated side members 54 and 56 and shorter end members 58 and 60. A downwardly extending groove 62 is provided in the elongated side member 54 while a similar downwardly extending groove 64 is provided in the other elongated side member 56. A bearing carrier block 66 similar to bearing carrier block 22 is mounted on end member 58 opposite downwardly extending groove 62 and a signal generator support plate 68 is attached to the end member 60 of the carriage frame 52 at the opposite end of groove 62 for providing support for an intermediate plate 63 on which a second rotary encoder 70 similar to the first rotary encoder 34 is mounted. As was noted previously, the rotary encoders 34 and 70 provide an output count in response to a predetermined amount of angular rotation (for example, 600 counts for each revolution in a first direction with reverse rotation decreasing the count in like manner).

Rotary encoder 70 is connected to a rotary drive rod 72 having a spiral groove 74. Rotary drive rod 72 is identical to the rotary drive rod 30 with the exception of the fact that it is of less axial length. A coupling 76 connects the end of the rotary drive rod to the rotary encoder 70 so that rotation of the rod 72 is conveyed to the input shaft of the encoder 70. Conventional indicator means 94 provides a visual indication of the amount of rotation of counter 70.

A first pin carrier block 80 is attached to the end member 58 of carriage frame 52 and is provided with an perture 82 through which the rotary drive rod 30 extends without contacting the surface of the aperture. Pin carrier block 80 includes a threaded bore in which a drive pin 84 is positioned. Drive pin 84 has a cylindrical end extension 86 dimensioned to extend into the spiral groove 38 when the pin is properly adjusted. Spiral groove 38 is oriented at a relatively large pitch angle with respect to the axis of rod 30 so that reactive force between the cylindrical end 86 of drive pin 84 and the groove results in rotation of the rod 30. Since the carriage frame 52 includes downwardly facing open cavities fittable over the slide bearings 42 and 48, the carriage is easily reciprocated on the rods 40 and 46 to provide a driving rotation of the rod 30 with a resultant generation of output signals from the generator encoder 34 being provided. It should be observed that a retainer 88 attached to end member 60 of the carriage frame 52 has a lower lip extending in a guide slot 90 extending along the length of one side of the fixed base frame 10. It should also be observed that downwardly facing grooves 90 and 92 are provided on the lower surface of the carriage frame 52 to fit over the slide bearing rods 40 and 46 without contacting same. Thus, the carriage frame 52 is easily and safely reciprocated in the direction of arrows 96 with the display 93 always indicating the position of the carriage along an axis parallel to the axes of rod 30 and slide bearing rods 40 and 46.

A slide bearing rod 100 extends along the length of the downwardly extending groove 62 of the elongated side member 54 and is supported at one end in the bearing carrier block 66 and at its other end in the signal generator support plate 68. Similarly, a slide bearing rod 102 is supported on rod support bracket plates 104 and 106 respectively positioned at opposite ends of the downwardly extending groove 64. Slide bearing sleeves 108 and 110 are mounted for reciprocation on the rod 100 and slide bearing sleeves 110 are similarly mounted on the rod 102. The slide bearing sleeves 108 and 110 are identical to the slide bearing sleeves 42 and 48. Slide bearing sleeves 108 and 110 provide support for a sensor carrier frame 112 including end members 114 and 116 connected by side members 118 and 120. Downwardly facing longitudinal slots 190 and 192 extend between the side members 118 and 120 and fit down over the polished slide bearing rods 100 and 102 as best shown in FIG. 5. Additionally, downwardly facing cylindrical apertures on the lower side of the sensor carrier frame 112 fit over the slide bearing sleeves 108 and 110 so that the sensor carrier frame 112 is capable of reciprocation in a second direction 98 perpendicular to the direction of movement 96 of the carriage frame 52.

A pin carrier block 122 is attached to the side member 120 and is basically identical to the pin carrier block 80. A drive pin 124 identical to drive pin 84 is positioned in the pin carrier block 122 for engagement of its cylindrical drive projection with the spiral groove 74 of the rotary drive rod 72. A retainer 126 is connected to side member 118 and has a lower protrusion 128 positioned in a slot 130 extending along the side of the elongated slide member 56 of the carriage frame 52. Retainer 126 is similar to retainer 88. Thus, it will be seen that reciprocation of the sensor carrier plate 114 in a second direction along an axis parallel to the axes of rods 72, 100, and 102 effects rotation of the rod 72 by driving engagement of the cylindrical tip on the end of drive pin 84 with spiral groove 74 to provide an output from the rotary encoder 70 with such actuating display 94 to indicate the transverse position of the carrier plate with respect to frame 10.

Three spacer members 132, 134 and 136 extend downwardly from the lower surface of the top plate 138 and position top plate 138 in relation to the sensor carrier frame 112 and are held in position by nuts 140, 142 and 146 respectively mounted on studs extending upwardly above and from spacers 132, 134 and 136. Spacer members 132, 134 and 136 each respectively have positioning pins 132', 134' and 136' extending downwardly into three of six bores 137 in the upper surface of sensor carrier frame 112 which permit the top plate 138 to also be held in a position rotated 180° from the illustrated position. A positioning block 160 rests on the upper surface of the top plate 138 and is held in position by a positioning pin 162 extending down through the positioning block into a selected one of positioning apertures 164 extending through the top plate as best shown in FIG. 3. Loss of the positioning pin 162 is prevented by a lanyard 166 held in position by nut 146. A yoke retainer 168 is connected to positioning block 160 by a screw 170. Yoke retainer 168 includes an axial bore 172 and consists of an upper larger diameter portion 174 and a smaller diameter portion 176 with the smaller diameter portion 176 extending downwardly into an aperture 180 provided in the top plate 138.

A support tube 184 of a yoke 182 extends upwardly into the bore 172 and is held in position by a set screw 186. Downwardly extending arms 194 and 196 of yoke 182 each respectively support pivot pins 198 and 200. Pivot pins 198 and 200 are respectively received in side ears 230 and 232 mounted in slots in a U-shaped adaptor retainer 202 having side plates 204 and 206 so that retainer 202 is pivotable about the aligned horizontal axes of pins 198 and 200. Adaptor retainer 202 supports a plastic transducer mount block 240 held in position by set screws 216 in side plates 204 and 206. Any of a wide variety of conventional transducers 242 can be mounted on the mount block 240.

A slide rod 210 has a pusher plate 212 connected to its lower end and has its upper end extending upwardly through the bore in support tube 184 with a coil spring 214 urging the pusher plate 212 downwardly against the top of the adaptor retainer 202 in a manner that will be obvious from inspection of FIG. 7.

The nature of the transducer 242 can vary in accordance with the particular scanning operation desired to be performed on the workpiece. For example, an ultrasonic transducer of conventional type capable of emitting sonic waves and detecting reflected waves for measuring the thickness of the workpiece or for detecting internal structural faults such as voids can be employed.

In operation the carriage can be manually reciprocated backwardly and forwardly on the slide bearing rods 40 and 42 in a first direction so as to provide a variable output from the rotary encoder 34 indicative of the position of the carriage along the axis parallel to the axis of rod 30 with the sensor carrier frame 112 similarly being capable of simultaneous movement in a second direction perpendicular to the first direction by virtue of its sliding support on the rods 100 and 102. Such last-mentioned movement is continuously monitored by the encoder 70. By having the encoders 34 and 70 connected to separate readout devices, such as displays 93 and 94, it is possible to provide the coordinates of any point over which the transducer is positioned at any particular time. Therefore, if the output from the transducer indicates that a void or other undesirable feature in the scanned workpiece has been detected, the user can simply look at the visual displays 93 and 94 and obtain the coordinates of the location of the void or the like. It is consequently possible to return to the workpiece at a later date and set up the equipment to move to the same coordinates to permit predetermination of the area containing the void so as to permit repairs to be effected.

It should be understood that the subject invention can be used on large bodies such as castings or the like by attaching it by use of the suction cups 16. Additionally, adaptor retainer 202 is capable of upward movement against the bias of spring 214 so as to be able to move over minor protuberances. Further, the apparatus can be used on curved surfaces as indicated in exaggerated manner in FIG. 6. When the device is being used with small bodies such as plate 300 illustrated in FIG. 4, such bodies can be held in clamped position by clamp screw clamps 302 and 304 as shown.

Thus, the device is capable of usage on large items and small items for detecting internal flaws so that the user need only know the coordinates of the detected flaws which can be relocated at a later time for repair or correction by repositioning the scanner in the same position on the body being scanned at the later time. The preferred embodiment is extremely rugged and reliable while providing substantial cost savings over automatic motor driven apparatus of the type previously employed for scanning purposes. Moreover, the present invention is more easily usable than the prior known devices since the transducer can be manually positioned in any particular location which the user may consider to be most likely to contain internal flaws. Considerable time savings in use of the device is therefore achieved.

It should be understood that numerous modifications of the preferred embodiment will undoubtedly occur to those of skill in the art and the spirit and scope of the invention is to consequently be limited solely by the appended claims.

I claim:

1. A manually operable scanner for movably supporting a sensor adjacent a body to be scanned for detecting characteristics of the body and for providing continuous signals indicative of the location of the sensor to provide an automatic indication of the location of sensed characteristics on the body, said scanner comprising portable frame means positionable adjacent a body to be scanned, carriage support means on said portable frame means supporting a carriage on said portable frame means for manually effected movement in either direction along a first axis, carrier means on said carriage for supporting a sensor carrier frame on said carriage for manually effected movement on said carriage in either a direction along a second axis perpendicular to said first axis, sensor means mounted on said sensor carrier frame, whereby said sensor means can be manually moved in any direction including a component of one or both of the first and second axes, a first encoder, a second encoder, said first and second encoders each providing an output count and having a rotary input shaft and counting up in response to rotation of its rotary input shaft in a first direction and counting down in response to rotation of its rotary input shaft in a reverse direction, a first mechanical drive connection between said carriage means and the rotary input shaft of said first encoder for continuously actuating said first encoder in response to manual movement of said carriage means in either direction along said first axis to continuously provide a first output count indicative of the position of said carriage means along said first axis at any given moment and a second mechanical drive connection between said sensor carrier frame and the rotary input shaft of said second encoder for continuously actuating said second encoder in response to manual movement of said sensor carrier frame in either direction along said second axis to continuously provide a second output count indicative of the position of said sensor carrier frame along said second axis at any given moment and monitoring means responsive to the count of said first and second encoders for providing a continuous indication of the coordinate position of said sensor means with respect to said portable frame means in response to movement of the sensor in any direction including directions canted to the said axes.

2. The invention of claim 1 wherein said first mechanical drive connection comprises a first rotary rod mounted on said portable frame means for rotation with its axis parallel to said first axis and including a spiral groove in its outer surface oriented at a relatively large pitch angle with respect to the axis of said first rotary rod, a first drive pin mounted on said carriage and engageable with said spiral groove for rotating said first rotary rod in response to manually effected movement of said carriage in either direction along said first axis.

3. The invention of claim 2 wherein said second mechanical drive connection comprises a second rotary rod mounted for rotation on said carriage with its axis parallel to said second axis and including a spiral groove in its outer surface oriented at a relatively large pitch angle with respect to the axis of said second rotary rod, a second drive pin mounted on said sensor carrier frame and engageable with said spiral groove in said second rotary rod for rotating said second rotary rod in response to manually effected movement of said sensor carrier frame in either direction along said second axis.

4. The invention of claim 1 wherein said sensor carrier frame comprises a hollow rectangular metal frame member, said carrier means on said carriage comprises first and second slide bearing rods mounted on said carriage, slide bearing member mounted on said first and second slide bearing rods for sliding movement thereon providing support for said sensor carrier frame, a horizontal top plate provided with a central aperture, a yoke retainer having a lower end positioned in said central aperture and including an axial vertically oriented bore, a yoke having a vertical support tube extending upwardly into said vertical bore and adjustably positioned therein, first and second downwardly extending arms on said yoke, pivot means mounted on the lower ends of said first and second arms providing support for a U-shaped adaptor retainer member having first and second parallel side plates, a transducer mount block mounted between said first and second side plates and providing support for said sensor and spring means for normally urging said sensor downwardly to a lower end of possible travel while permitting upward movement of said transducer mount block to a limited extent.

5. The invention of claim 1 wherein said carrier means includes a top plate to which said sensor is mounted, a carrier frame having an upper surface including a plurality of vertical bores for receiving positioning pins extending downwardly from the top plate with said bores being located so that one group of said bores receives said positioning pins when said top plate is in a first position and another group of said bores receives said positioning pins when said top plate is in a second position oriented 180° from its first position.

6. The invention of claim 5 wherein said first mechanical drive connection comprises a first rotary rod mounted on said portable frame means for rotation with its axis parallel to said first axis and including a spiral groove in its outer surface oriented at a relatively large pitch angle with respect to the axis of said first rotary rod, a first drive pin mounted on said carriage and engageable with said spiral groove for rotating said first rotary rod in response to manually effected movement of said carriage in either direction along said first axis.

7. The invention of claim 6 wherein said second mechanical drive connection comprises a second rotary rod mounted for rotation on said carriage with its axis parallel to said second axis and including a spiral groove in its outer surface oriented at a relatively large pitch angle with respect to the axis of said second rotary rod, a second drive pin mounted on said sensor carrier frame and engageable with said spiral groove in said second rotary rod for rotating said second rotary rod in response to manually effected movement of said sensor carrier frame in either direction along said second axis.

* * * * *